United States Patent [19]
Harges, Jr. et al.

[11] Patent Number: 5,628,308
[45] Date of Patent: May 13, 1997

[54] HEAT AND FIRE RESISTANT RESPIRATORY FILTRATION MASK

[76] Inventors: Cordell F. Harges, Jr., 12629 Loma Verde Dr., Victorville, Calif. 92392; Bert Rivera, 1135 Wilcox Ave., Monterey Park, Calif. 91755

[21] Appl. No.: 297,937

[22] Filed: Aug. 31, 1994

Related U.S. Application Data

[63] Continuation-in-part of Ser. No. 183,417, Jan. 19, 1994, abandoned.

[51] Int. Cl.⁶ .................. A62B 18/02; A42B 1/00; A61F 9/00; A61F 11/00
[52] U.S. Cl. .................. 128/206.21; 128/206.17; 128/206.28; 128/207.11; 128/857; 128/201.25; 2/7
[58] Field of Search .................. 128/201.22–201.25, 128/206.19, 206.12, 206.17, 206.21, 206.23, 206.24, 206.27–207.12, 857; 2/2, 5, 7, 84, 203, 202, 205

[56] References Cited

U.S. PATENT DOCUMENTS

| | | | |
|---|---|---|---|
| 695,403 | 3/1902 | Longden | 128/206.12 |
| 996,739 | 7/1911 | Vinton | 128/201.23 |
| 2,008,677 | 7/1935 | Booharin | 128/206.17 |
| 4,231,118 | 11/1980 | Nakagawa | 2/7 |
| 4,297,117 | 10/1981 | Holter et al. | 128/205.27 |
| 4,520,509 | 6/1985 | Ward | 128/206.28 |
| 4,573,217 | 3/1986 | Reed | 2/7 |
| 4,637,383 | 1/1987 | Lopez | 128/201.25 |
| 4,683,880 | 8/1987 | Werjefet | 128/201.23 |
| 4,688,567 | 8/1987 | Kikuchi et al. | 128/206.17 |
| 4,771,771 | 9/1988 | Walther | 128/201.25 |
| 4,870,959 | 10/1989 | Reisman et al. | 128/201.22 |
| 4,998,529 | 3/1991 | Werjefet | 128/201.13 |
| 5,003,974 | 4/1991 | Mou | 128/205.27 |
| 5,035,006 | 7/1991 | Hetz et al. | 2/203 |
| 5,040,530 | 8/1991 | Bauer et al. | 128/201.25 |
| 5,058,211 | 10/1991 | Hanks | 2/206 |
| 5,119,808 | 6/1992 | Marquandt et al. | 128/201.22 |
| 5,140,980 | 8/1992 | Haughey et al. | 128/201.25 |
| 5,265,669 | 11/1993 | Schneider | 165/46 |
| 5,291,880 | 3/1994 | Almovist et al. | 128/206.24 |
| 5,315,987 | 5/1994 | Swann | 128/201.25 |
| 5,322,060 | 6/1994 | Johnson | 128/205.27 |

*Primary Examiner*—Kimberly L. Asher
*Attorney, Agent, or Firm*—Rothwell, Figg, Ernst & Kurz

[57] ABSTRACT

A heat and fire resistant respiratory filtration mask is specially adapted for protecting firefighters in wildland/brush fire environments. The mask is fabricated of heat and fire resistant material and includes facilitated fasteners for attachment to the head and face of the user. A respiratory filtration pocket is provided for accommodation of a respiratory filtration element such as a fiber filter. The pocket has a closable slit for accessing the filter for removal and replacement. The mask includes openings for exhalation valves of filtration elements and openings for ventilation through the nose and mouth of the wearer. Alternatively, inhalation and exhalation orifices are provided to accommodate a canister-type filter, with a filter cartridge of the canister-type filter also functioning as a fastener to the mask. In a preferred embodiment the mask is elongated to provide heat and flame protection to the neck as well as the entire facial area below the eyes.

11 Claims, 9 Drawing Sheets

HEAT AND FIRE RESISTANT RESPIRATORY FILTRATION MASK

CROSS REFERENCE TO RELATED APPLICATION

This application is a continuation-in-part of application Ser. No. 08/183,417 filed Jan. 19, 1994, now abandoned.

BACKGROUND OF THE INVENTION

1. Field of the Invention

This invention relates generally to protective apparel, and more specifically relates to respiratory filtration apparel for firefighters that is also heat and fire resistant.

2. Background and Prior Art

Firefighters must deal with two distinct types of firefighting: interior or structural firefighting where a firefighter enters a building or other structure to extinguish a flame that is for the most part contained within the building, and brush or wildland firefighting where the firefighter must contend with rapidly spreading flames, high wind conditions and often rough terrain.

While providing safety equipment for firefighters has been of concern for some time, most of the developments have concentrated on equipment for interior or structural firefighting. For example, conventional breathing apparatus and protective hood gear, well-suited to structural firefighting, are ineffective and/or impractical for fighting brush or wildland fires. Conventional breathing apparatus for interior firefighting is much too cumbersome for brush fires where a vast and typically rough terrain must be covered and negotiated rather quickly to prevent the fire from spreading. Protective hood gear made of flame resistant material such as Nomex, an example of which is shown in U.S. Pat. No. 4,573,217, is constructed for use with such breathing apparatus and does not by itself provide any respiratory air filtration or heat protection for the face. Additionally, this type of hood is loose-fitting around the face, allowing flying ash and burning embers to enter the space between the hood and the face, causing burning and consequent scarring.

Thus, the options heretofore available for protection in brush/wildland firefighting have been limited to the use of a simple cotton or cotton blend bandanna worn over the nose and mouth and tied behind the neck in a knot. The cotton bandanna provides only minimal protection from smoke and particulate inhalation and provides no heat or flame protection at all. Indeed, instances have been reported of such bandannas actually catching on fire themselves while worn in brush firefighting.

Improvements to the conventional cotton bandanna have been attempted. One known product is an anti-pollutant bandanna made of a cotton blend material having an activated charcoal cloth filter sewn directly on the inside thereof. This product has an exposed aluminum nose pinch attached to the top portion which fits over the bridge of the user's nose. The bandanna is secured to the user's head by tying a knot behind the neck. This product provides only minimal protection from smoke and no protection from heat and flame.

Another known filtration mask is made of neoprene, a rubberlike insulation material commonly used in the manufacture of wetsuits for scuba diving. Cut-outs or holes are provided in the front of the mask for inhalation since neoprene does not allow air exchange because of its density. Exhalation is enabled through the use of exhalation valves provided on the mask in the location of the user's mouth. This mask also includes an activated carbon filter attached directly to the inside portion of the mask. The neoprene material is not heat or fire resistant and is subject to melting under high heat conditions. Both of the above known products cover only the nose, mouth and chin areas of the face, leaving the lower chin, neck, and upper facial areas exposed.

Other known bandanna-type garments are shown in U.S. Pat. Nos. 5,035,006 and 5,058,211. However, these garments are not designed for firefighting environments and offer little or no protection under such circumstances.

Consequently, there exists a need in the art for a simple, lightweight protective mask that will provide a high degree of heat and flame resistant protection while also providing protection from smoke and other particulate inhalation for firefighters in the fighting of brush or wildland fires and which can be put on rapidly as the need arises.

SUMMARY OF THE INVENTION

The present invention overcomes the deficiencies in the prior art and provides a solution to the need for protection in fighting wildland/brush fires, by providing a simple, lightweight, yet highly effective heat and fire resistant respiratory filtration mask that is easily attached and worn by a firefighter under such circumstances.

The present invention provides heat and flame protection of the facial area while also providing respiratory filtration of smoke and other air pollutants associated with wildland/brush fires. The respiratory filtration mask of the present invention allows the wearer to use his or her choice of filtration element with the mask and enables the wearer to easily replace a dirty filtration element on the scene of a brush fire as needed. The respiratory filtration mask according to the invention utilizes hook-and-loop fastener material, such as Velcro® or other equivalent material, to enable the mask to be both quickly secured to the face of the wearer as well as quickly removed, without the need to tie or untie a knot behind the neck. The inventive respiratory mask according to the invention is also more cost-effective for purchasers by providing a "one-size-fits-all" mask that provides economy of use.

The present invention achieves such advantages by providing a heat and fire resistant protective mask, comprising a heat and fire resistant main portion adapted to cover at least the nose and mouth of a wearer, first and second heat and fire resistant flap portions extending from the main portion and adapted to be fastened around the neck of the wearer, and an air filtration pocket provided in the main portion including means for removably inserting a replaceable respiratory air filter therein. The pocket of the mask is accessed by a slit portion provided with a fastener such as the hook-and-loop fastener.

The present invention further provides a heat and fire resistant protective mask, comprising an outer shell made of heat and fire resistant material and having a main portion adapted to cover the nose, mouth, neck, and upper and lower cheekbone areas of a wearer, and first and second flap portions adapted to be fastened around the neck of the wearer, an inner liner made of heat and fire resistant material attached to the outer shell, a pocket formed between the outer shell and the inner liner, and a respiratory air filter provided in the pocket.

BRIEF DESCRIPTION OF THE DRAWINGS

The present invention will become more fully understood from the detailed description given hereinbelow and the accompanying drawing, which is given for purposes of illustration only and is not limitative of the present invention, and wherein.

DETAILED DESCRIPTION OF THE PREFERRED EMBODIMENT

Figure 1:
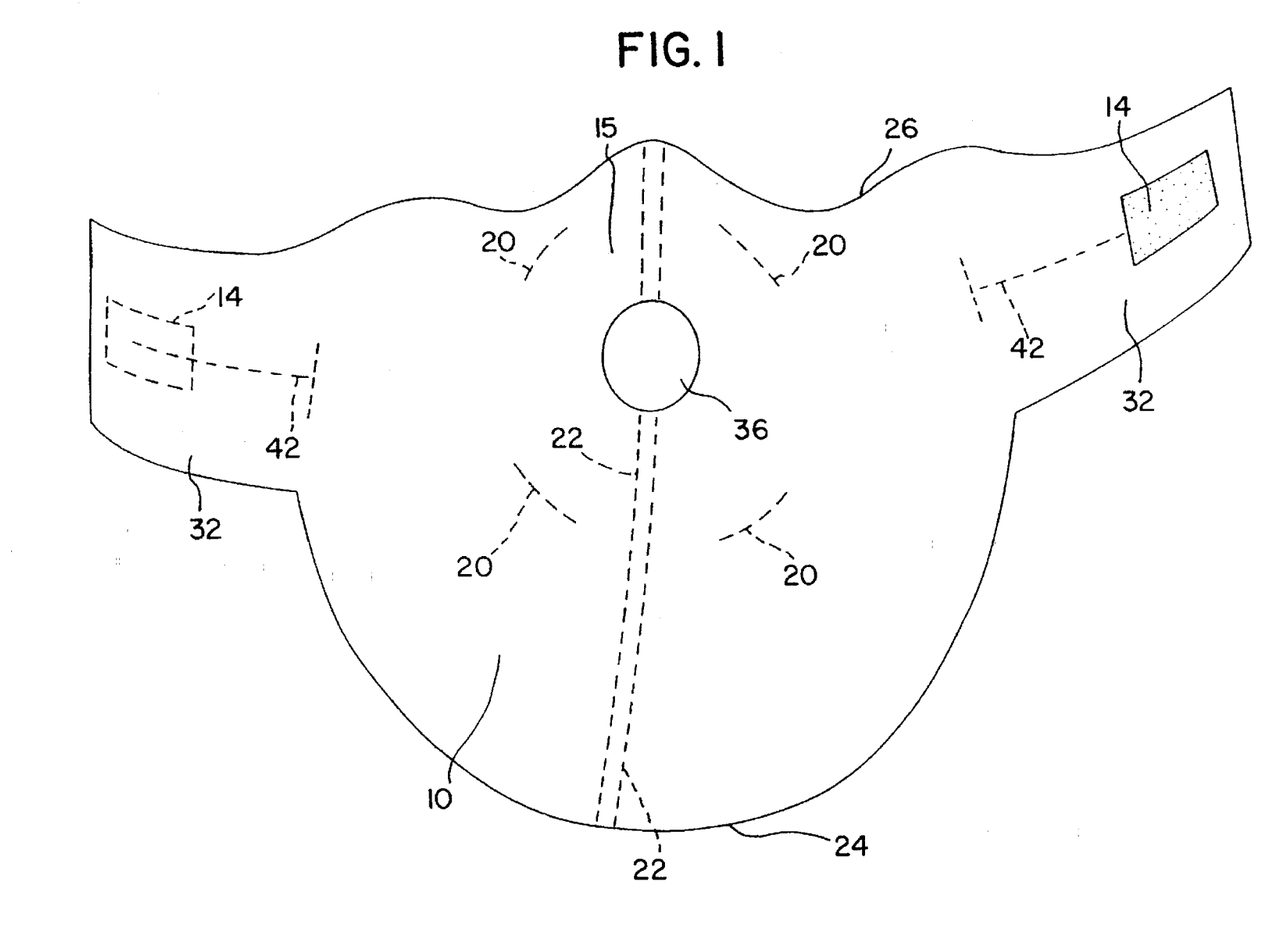
FIG. 1 is a front view of the outer shell of the respiratory filtration mask according to a first embodiment of the present invention.
Figure 2:
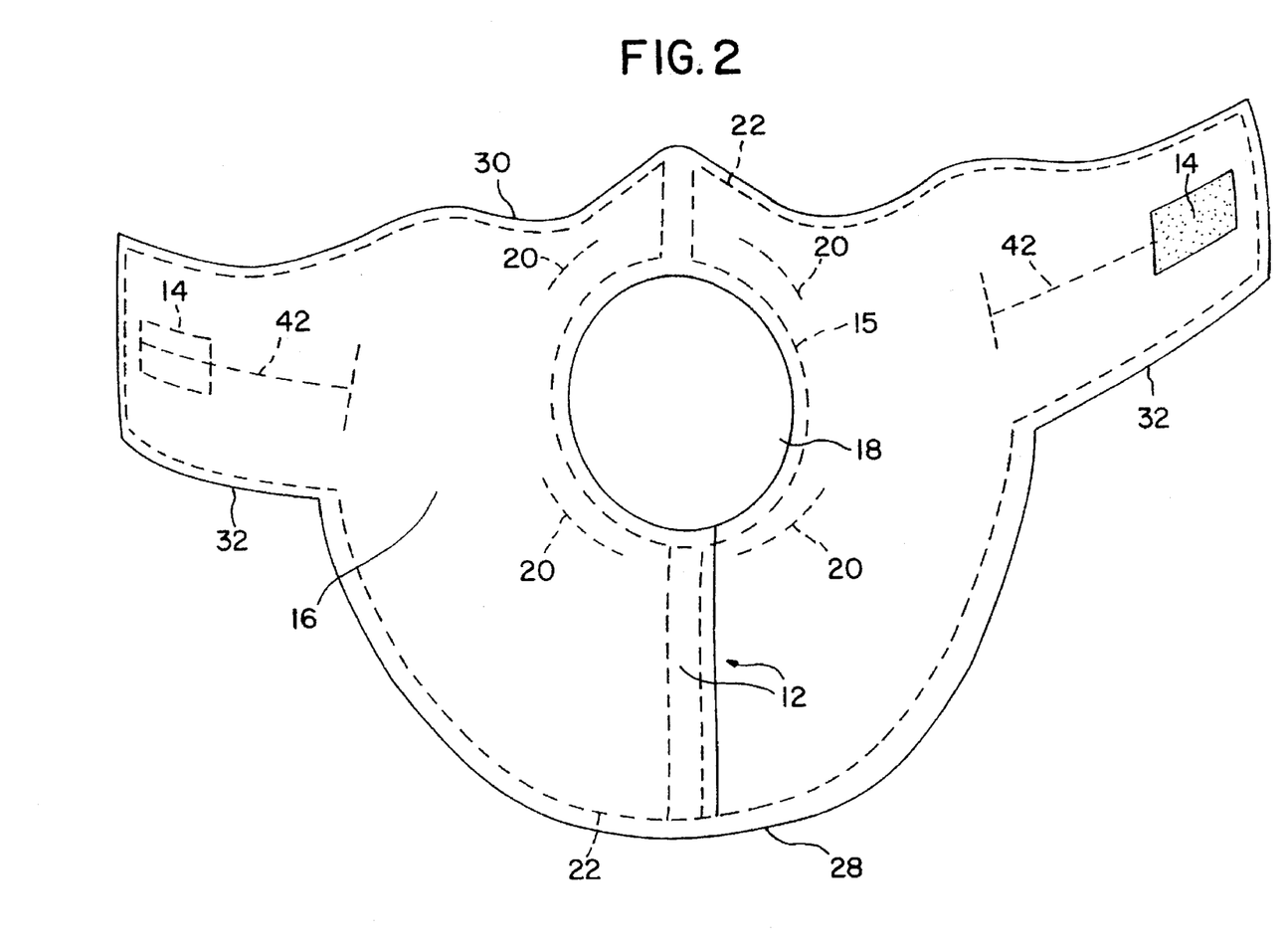
FIG. 2 is a front view of the inner liner of the respiratory filtration mask of the first embodiment.

The present invention will now be described in detail with reference to the accompanying FIGS. 1–8. FIG. 1 shows a front view of the outer shell 10 of the respiratory filtration mask according to one preferred embodiment of the invention. The outer shell is made of heat and fire resistant material, such as Nomex, PBI, Kevlar, Nomex/Kevlar blend, or other equivalent material. The outer shell may also be constructed of ballistic (bulletproof) material such as ballistic Kevlar, for additional protection from gunfire in hazardous conditions such as riot environments. The outer shell has a main portion 24 which covers the nose, mouth, neck, and upper and lower cheekbone areas of the wearer. The top of the outer shell 26 is contoured to fit under the orbits of the eye sockets to provide maximum protection to the face while preserving an adequate field of vision for the wearer. Flap portions 32 extend from the main portion 24 and are adapted to be secured around the back of the neck. Fasteners 14 are provided for this purpose, and preferably are constituted by hook-and-loop type fastener material. However, other fasteners such as snaps, buckles or hooks may be equivalently used. Referring to FIG. 2, it is seen that one fastener 14 is attached to the outer shell 10 and the other fastener 14 is attached to the inner liner 16, so that the fasteners 14 are coupled together at the back of the neck. The inner liner 16 is also preferably made of fire resistant material, but may be made of other materials in other embodiments of the invention.

The flap portions 32 are provided with elastic stitching 42 for elastic material 44 inserted between the outer shell and inner liner (see FIG. 3) which provides a snug fit around the facial area to prevent penetration of heat and air pollutants under the mask. A respiratory filtration pocket 15 is formed between the outer shell 10 and the inner liner 16 by sewn-in seams 20. The outer shell 10 includes an opening 36 to accommodate an air filter element exhalation valve, while the inner liner 16 includes a larger ventilation orifice 18 which fits the installed filtration element over the nose and mouth of the wearer for filtered respiration. As shown in FIG. 2, the inner liner 16 is provided with a slit section 12 for facilitating insertion and removal of the air filtration element into and from the filtration pocket 15. Slit section 12 extends toward the bottom 28 of the inner liner 16. This slit section 12 is also provided with fasteners, preferably hook-and-loop, to secure the filtration element in place. The fasteners for the slit section 12 may be constituted by other fastening mechanisms such as snaps, buckles or hooks. The filtration pocket is sized to accommodate various types of filters, such as dust and fume fiber mask filters or canister-type filters. Examples of such filters are the 3M fiber mask filter No. 9925 and the 3M 6000 Series canister-type respirator.

Figure 3:
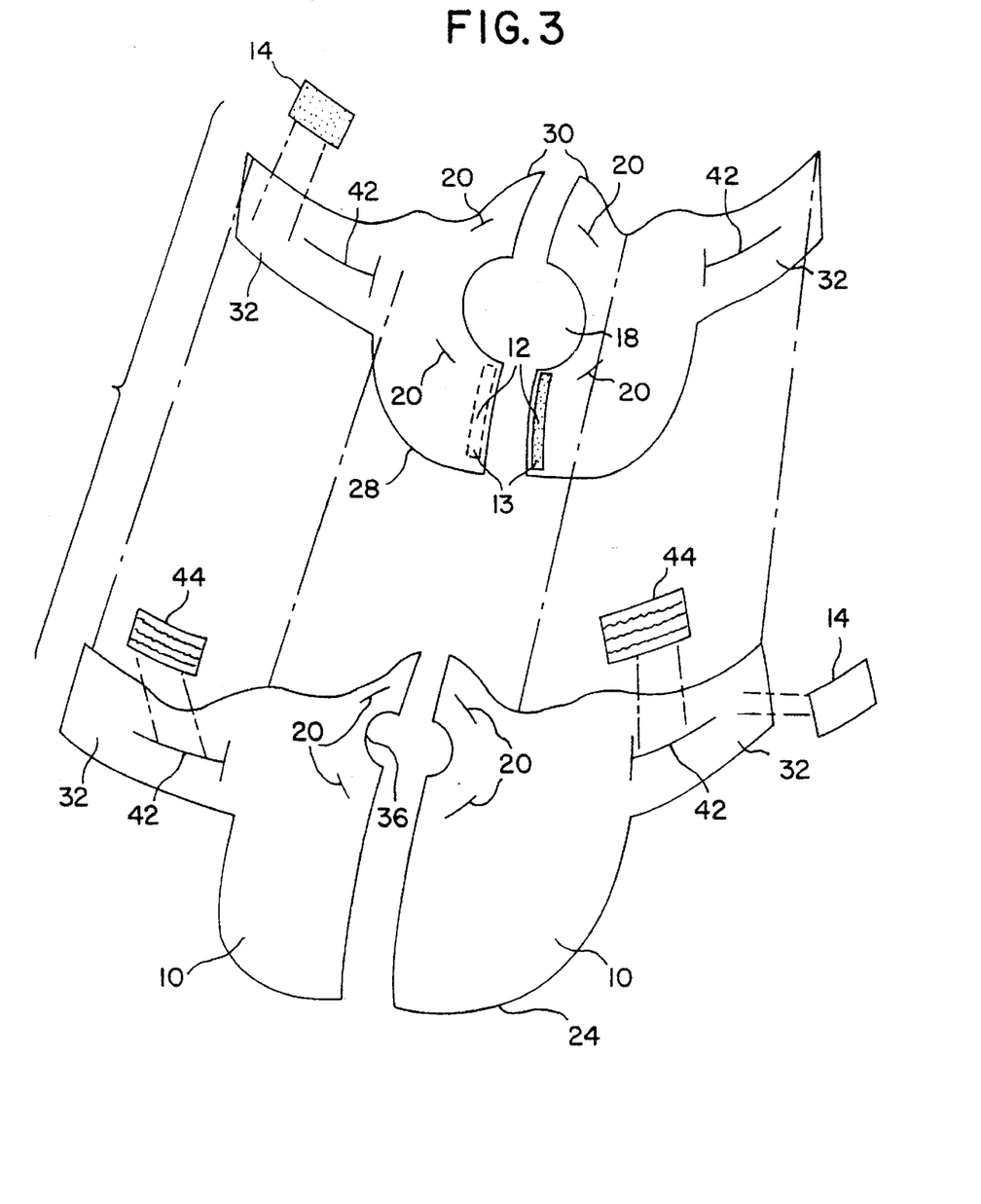
FIG. 3 is an exploded view of the respiratory filtration mask of the first embodiment illustrating the details of construction.

FIG. 3 shows in exploded view the details of the construction of the heat and fire resistant respiratory filtration mask according to one preferred embodiment of the invention. As shown the outer shell and inner liner may be fabricated from symmetrically cut sections of fire resistant material and sewn together by stitching 22 (see FIGS. 1 and 2). However, it is contemplated that the outer shell and inner liner may be equivalently formed of an integral piece of material. FIG. 3 further shows the details of the fastener material 13 attached to the slit section 12 of the inner liner for access to the air filtration pocket.

Figure 9:
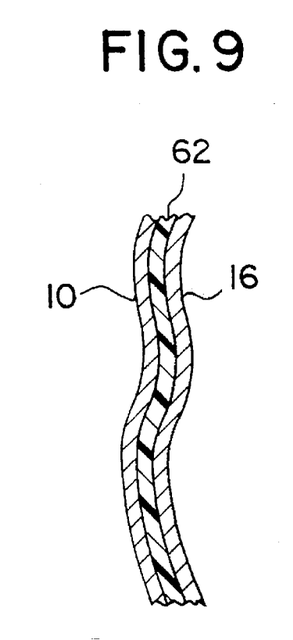
FIG. 9 is a cutaway cross-sectional view of an alternative embodiment of the invention including a thermal vapor barrier.

An alternative embodiment of the invention is shown in FIG. 9, wherein a thermal vapor barrier 62 is installed between the outer shell 10 and the inner shell 16. The barrier 62 is made of material, such as thin plastic which is impervious to vapors and will prevent vapors from permeating through the mask to the skin of the user.

Figure 4:
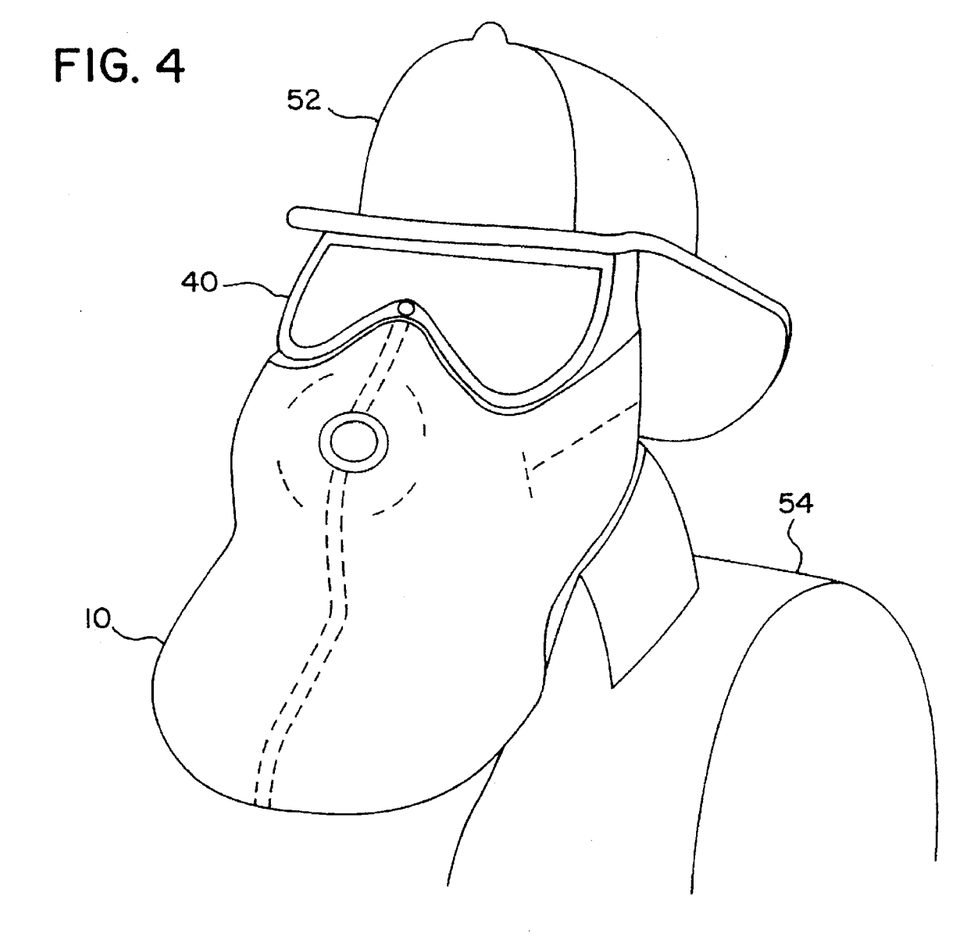
FIG. 4 is a plan view of the respiratory filtration mask of the first embodiment as worn by a firefighter.

FIG. 4 illustrates the use of the inventive heat and fire resistant respiratory filtration mask 10 of the present invention with safety goggles 40, helmet 52, and brush coat 54. As seen from the figure, the respiratory filtration mask 10 provides heat and flame protection for the entire facial area under the eyes, including the upper cheekbone areas as well as the lower chin and neck areas. However, it is contemplated that the mask may be configured in a shorter version without the additional neck protection, but otherwise providing the improved protection afforded by the preferred embodiment.

Figure 10:
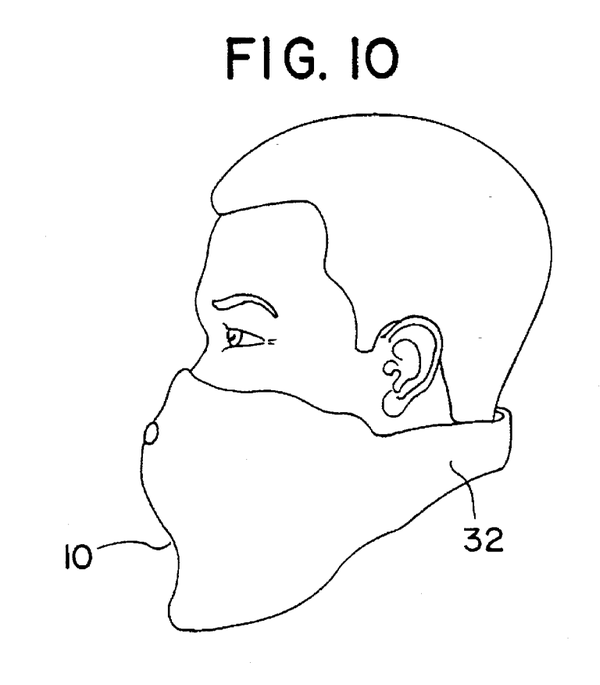
FIG. 10 is a side view of the respiratory filtration mask 10 according to one embodiment of the invention.

FIG. 10 shows a side view of the respiratory filtration mask 10, illustrating the neck coverage of the flap portion 32 around the neck of the wearer.

A second embodiment of the invention will now be described with reference to FIGS. 5–8 in which like elements are given like reference numerals. The heat and flame resistant filtration mask 10a of the second embodiment of the invention is especially adapted to accommodate canister-type respiration filters such as the 3M 6000 Series or any other equivalent type of canister filter. Such a filter is illustrated in FIG. 7 as filter 48. The filter 48 is provided with two inhalation valves 50 and an exhalation valve 56.

Figure 5:
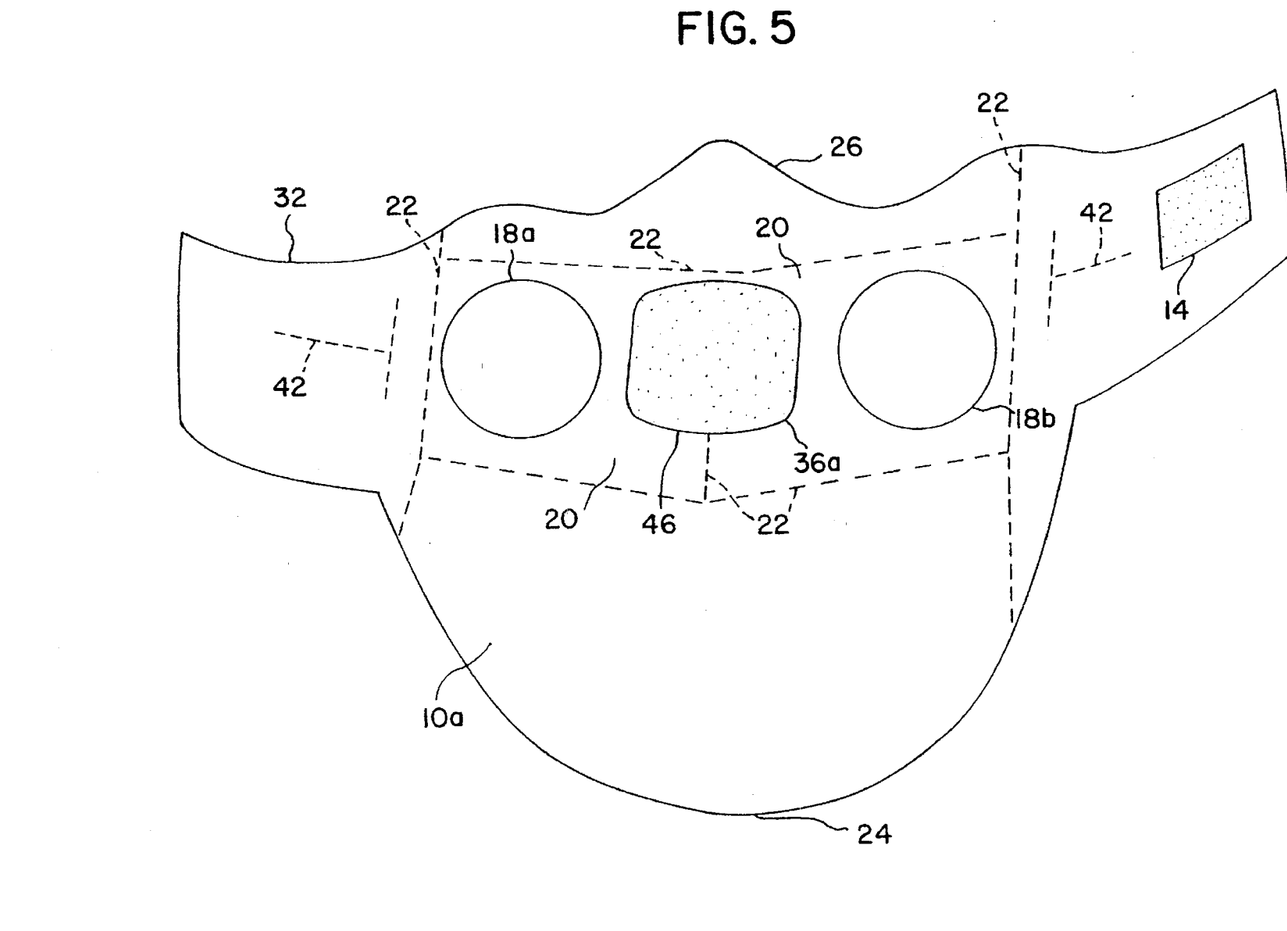
FIG. 5 is a front view of the outer shell of a respiratory filtration mask according to a second embodiment of the present invention.
Figure 6:
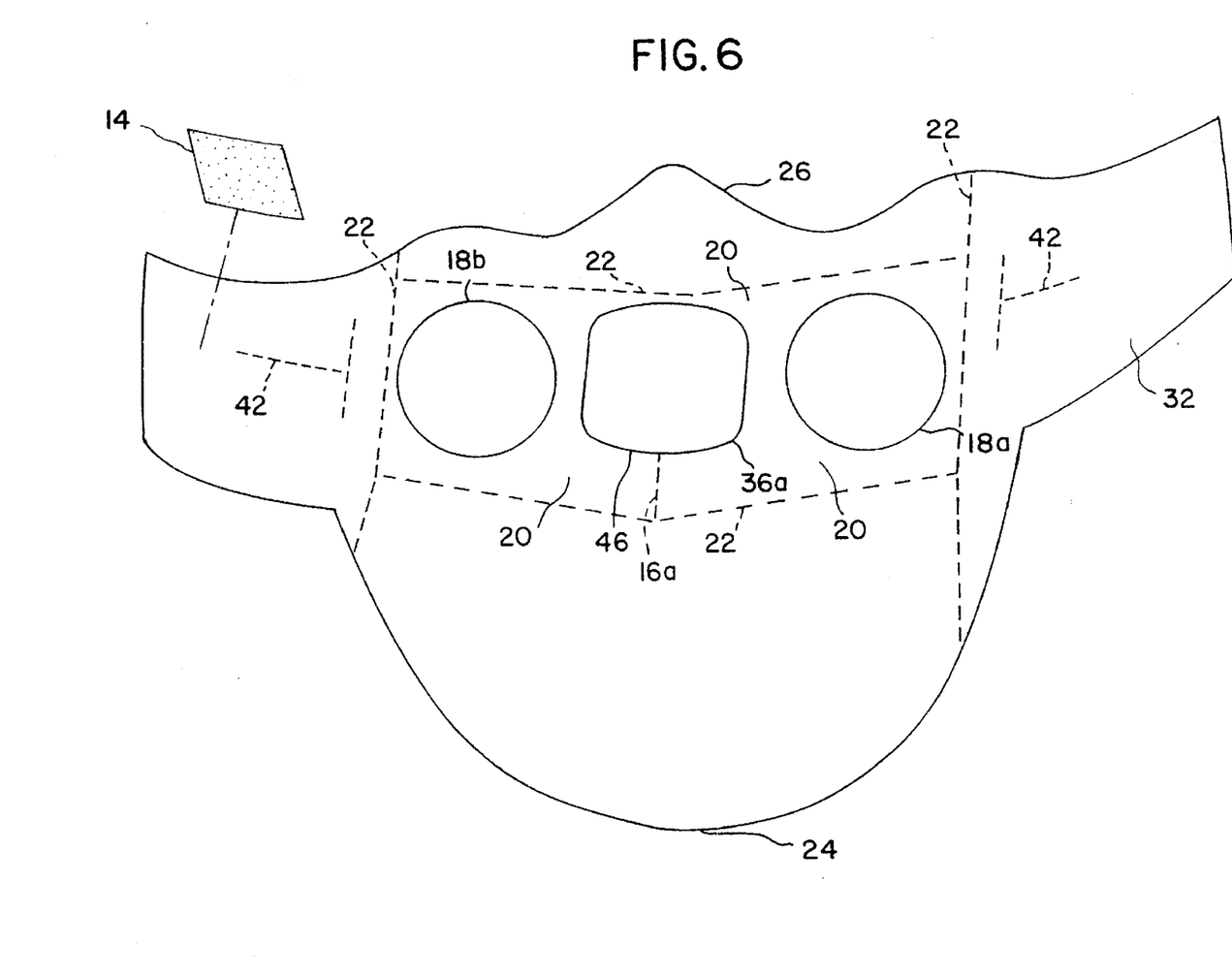
FIG. 6 is a front view of the inner liner of the second embodiment of the invention.
Figure 7:
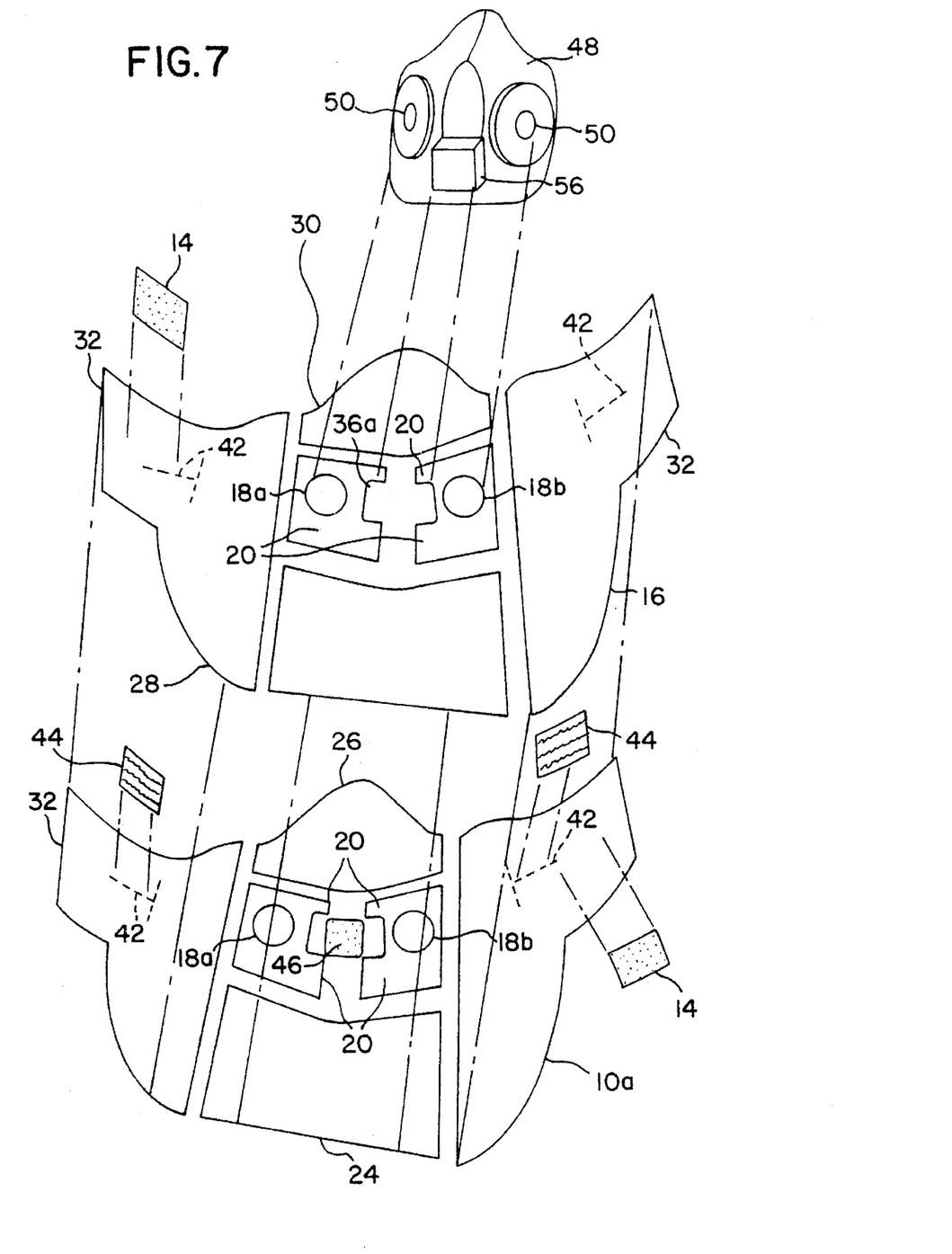
FIG. 7 is an exploded view of the respiratory filtration mask according to the second embodiment of the invention illustrating the details of construction.
Figure 8:
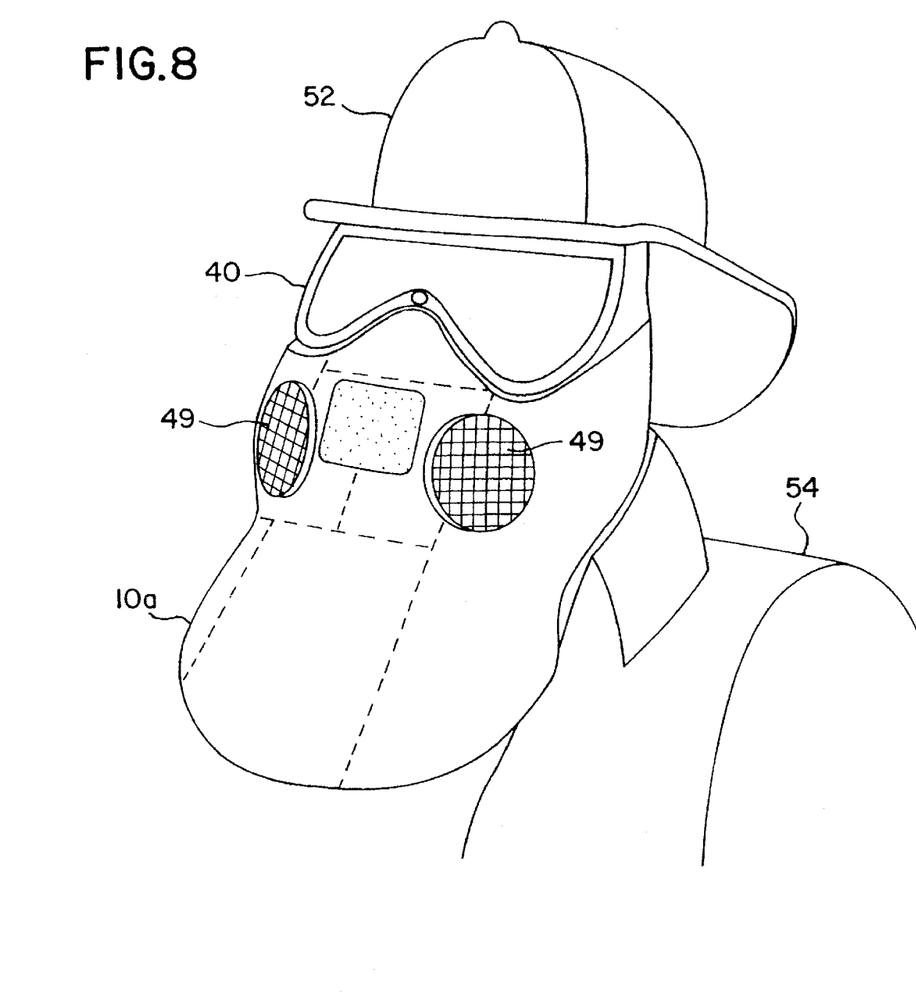
FIG. 8 is a plan view of the respiratory filtration mask of the second embodiment as worn by a firefighter.

According to the second embodiment of the invention, two inhalation orifices 18a and 18b are provided in the outer shell 10a and inner liner 16a, as shown in FIGS. 5 and 6 respectively, through which the inhalation valves 50 are inserted. A central exhalation orifice 36a is provided between the orifices 18a, 18b to accommodate the exhalation valve 56 of the mask (see FIG. 7). As shown in FIG. 8, filtration cartridges 49 are installed over the inhalation valves 50 through the orifices 18 so as to secure the filter 48 to the heat and flame resistant mask to by sandwiching mask between the main body of the filter 48 and the filtration cartridges 49. The cartridges 49 attach to the inhalation valves 50 through a bayonet-type twist-and-lock connection. An additional attachment (not shown) may be provided to further secure the filter 48 to the inner liner 16*a* of the mask in the form of hook-and-loop fasteners attached respectively to the front of the filter 48 and to the inner liner 16*a*. A porous, fire retardant exhalation valve cover 46 as shown in FIG. 5 may be provided to protect the exhalation valve 56 (see FIG. 7).

According to the second embodiment of the invention, the outer shell 10*a* and inner liner 16*a* are sewn together around the inhalation orifices 18*a*, 18*b* and the exhalation orifice 36*a* via stitching seams 22. Since the respiration filter may be secured to the flame resistant mask through the use of the filter cartridges as fastening means, it is not necessary to provide a filter pocket between the outer shell and the inner liner. The flame resistant respiratory filtration mask according to the second embodiment thus provides two layers of protection for the respiration filter against heat and flame. Additionally, because the inner liner is located on the same side of the respiration filter as the outer shell, the enhanced seal attained between the canister-type respirator and the mouth, nose and chin is not compromised.

The invention having been thus described, it will apparent to those skilled in the art that the same may be varied in many ways without departing from the spirit and scope of the invention. Any and all such modifications are intended to be covered by the following claims.

What is claimed is:

1. A heat and fire resistant protective mask, comprising:
   a main portion adapted to cover at least the nose, mouth, neck and cheekbone areas of a wearer, and first and second flap portions extending from either side of said main portion and adapted to be fastened around the neck of the wearer;
   said main portion and said flap portions each comprising an outer shell made of a heat and fire resistant material and an inner liner made of heat and fire resistant material coextensive with and attached to said outer shell;
   means for supporting in a removable manner a respiratory air filter between said inner liner and said outer shell; and
   a respiratory air filter.

2. A heat and fire resistant protective mask as set forth in claim 1, further comprising fastener means provided on said first and second flap portions of said outer shell and said inner liner for securing said first and second flap portions around the neck of the wearer.

3. A heat and fire resistant protective mask as set forth in claim 2, wherein said fastener means comprises hook-and-loop fastener material.

4. A heat and fire resistant protective mask as set forth in claim 1, wherein said means for supporting said respiratory filter comprises an elongated slit section in said inner liner of said main portion provided with fastener means for opening and closing said slit section for insertion and removal of said respiratory air filter between said outer shell and said inner liner.

5. A heat and fire resistant protective mask as set forth in claim 1, wherein said main and flap portions of said outer shell are made of ballistic material.

6. A heat and fire resistant protective mask as set forth in claim 1, further comprising a thermal vapor barrier installed between said outer shell and said inner liner.

7. A heat and fire resistant protective mask, comprising:
   a main portion adapted to cover at least the nose, mouth, neck and cheekbone areas of a wearer, and first and second flap portions extending from either side of said main portion and adapted to be fastened around the neck of the wearer;
   said main portion and said flap portions each comprising an outer shell made of a heat and fire resistant material and an inner liner coextensive with said outer shell made of a heat and fire resistant material; and
   a respiratory air filter unit having at least one inhalation valve, an exhalation valve, and a filter cartridge removably attachable to said at least one inhalation valve;
   said outer shell main portion and said inner liner main portion each including a first orifice for accommodating said exhalation valve of said respiratory air filter, and at least a second orifice for accommodating said at least one inhalation valve of said respiratory air filter unit.

8. A heat and fire resistant protective mask as set forth in claim 7, further comprising fastener means provided on said first and second flap portions of said outer shell and said inner liner for securing said first and second flap portions around the neck of the wearer.

9. A heat and fire resistant protective mask as set forth in claim 8, wherein said fastener means comprises hook-and-loop fastener material.

10. A heat and fire resistant protective mask as set forth in claim 7, wherein said respiratory air filter unit includes a second inhalation valve and a second filter cartridge removably attachable to said second inhalation valve, and wherein said outer shell main portion and said inner liner main portion each include a third orifice for accommodating said second inhalation valve of said respiratory air filter unit.

11. A heat and fire resistant protective mask as set forth in claim 7, wherein said main and flap portions of said outer shell are made of ballistic material.

* * * * *